US008748173B2

(12) United States Patent
Kearney

(10) Patent No.: US 8,748,173 B2
(45) Date of Patent: Jun. 10, 2014

(54) MONOCLONAL ANTIBODIES SPECIFIC FOR ANTHRAX SPORES AND PEPTIDES DERIVED FROM THE ANTIBODIES THEREOF

(75) Inventor: John F. Kearney, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 823 days.

(21) Appl. No.: 11/601,133

(22) Filed: Nov. 17, 2006

(65) Prior Publication Data
US 2007/0259387 A1 Nov. 8, 2007

Related U.S. Application Data

(63) Continuation of application No. 11/171,518, filed on Jul. 1, 2005, now abandoned, which is a continuation of application No. 09/069,628, filed on Apr. 29, 1998, now Pat. No. 6,913,756.

(51) Int. Cl.
*A61K 39/40* (2006.01)
*G01N 33/40* (2006.01)
*C12N 5/12* (2006.01)
*C12N 9/52* (2006.01)

(52) U.S. Cl.
USPC .................. 435/340; 424/130.1; 424/143.1; 424/150.1; 424/164.1; 424/184.1; 424/234.1; 424/246.1; 435/41; 435/243; 435/320.1; 435/325; 435/329

(58) Field of Classification Search
CPC ........... C07K 16/1278; C07K 2317/00; C07K 2317/30; C07K 2317/70; G01N 33/56911; G01N 2333/32; A61K 2039/505; A61K 2039/6056
See application file for complete search history.

(56) References Cited

U.S. PATENT DOCUMENTS

| 5,223,409 | A | | 6/1993 | Ladner et al. |
| 5,254,799 | A | * | 10/1993 | De Greve et al. ............. 800/302 |
| 5,256,532 | A | * | 10/1993 | Melnicoff et al. ................ 435/5 |
| 5,686,113 | A | | 11/1997 | Speaker et al. |
| 5,753,222 | A | | 5/1998 | Marrone et al. |
| 5,866,430 | A | * | 2/1999 | Grow ............................... 506/6 |
| 6,913,756 | B1 | | 7/2005 | Kearney |
| 2003/0044838 | A1 | | 3/2003 | Turnbough et al. |
| 2007/0020281 | A1 | | 1/2007 | Kearney |
| 2007/0281302 | A1 | | 12/2007 | Turnbough et al. |

FOREIGN PATENT DOCUMENTS

| WO | PCT/US99/09122 | 4/1999 |
| WO | WO 9955842 | 11/1999 |

OTHER PUBLICATIONS

Ezzell et al., (1990. J. of Clin. Micriobio. vol. 28(2):223-231).*
Quinlan et al., (1997. Applied & Environ. Microbio. vol. 63(2): 482-487).*
Williams et al., 2003. Applied & Environ. Microbio. vol. 69(10): 6288-6293.*

(Continued)

*Primary Examiner* — Ja'Na Hines
(74) *Attorney, Agent, or Firm* — Ballard Spahr LLP

(57) ABSTRACT

The present invention provides monoclonal antibodies which are highly specific for *Bacillus* spores. Also provided are peptides derived from those monoclonal antibodies. Both the antibodies and peptides are highly specific and can discriminate between spores of potentially lethal organisms such as *Bacillus anthracis* and other harmless but closely related *bacilli* and provide a very powerful tool in the construction of detection instruments as counter measures.

5 Claims, 9 Drawing Sheets

Antibodies with different reactivities for spores

Ungerminated

Germinated

F12(2)　　A03(16)　　B05(2)　　C10(33)　　E12(10)

(56) References Cited

OTHER PUBLICATIONS

Radnedge et al., 2003. Applied & Environ. Microbio. vol. 69(5): 2755-2764.*

Phillips et al. (FEMS Microbio Immunology. 1988. vol. 47 (3): 169-178).*

Phillips et al., (J. of Applied Bacteriol. 1988. vol. 64:47-55).*

D'Mello, "Definition of the Primary Structure of Hepatitis B Virus (HBV) pre-S Hepatocyte Binding Domain Using Random Peptide Libraries," *Virology*, 237, 319-326 (1997).
Ezzell, "Identification of *Bacillus anthracis* by Using Monoclonal Antibody to Cell Wall Galactose-N-Acetylglucosamine Polysaccharide," *Jml. of Clinical Microbiology*, 28(2): 223-231 (1990).
Little, et al., "Comparative Efficacy of *Bacillus-anthracis* Live Spore Vaccine and Protective Anitgen Vaccine Against Anthrax in the Guinea-Pig," *Infect. and Immun.*, 53(2):509-512, XP002919475 (1986).
Quinlan, et al., "Monoclonal Antibodies for Use in Detection of *Bacillus* and *Clostridium* Spores," *Appl. Environ. Micrbio.*, 563(2):482-487 (1997).
Radnedge, et al., "Genome Differences That Distinguish *Bacillus anthracis* From *Bacillus cereus* and *Bacillus thuringiensis," Appl. Environ. Micrbio.*, 69(5):2755-2764 (2003).
Walker, et al., "Immunology of Spore and Sporeforms, Antigens of the Spore and Location of Spore and Vegetative Antigens With Labeled Antibodies," *Spores*, 5:321-337 (1972).
Williams, et al., "Species-Specific Peptide Ligands for the Detection of *Bacillus anthracis* Spores," *Appl. Environ. Micrbio.*, 69(10):6288-6293 (2003).
U.S. Appl. No. 09/069,628, Kearney, filed Apr. 29, 1998, Amendment after Notice of Allowance (Rule 312), Jul. 16, 2004.
U.S. Appl. No. 09/069,628, Kearney, filed Apr. 29, 1998, Notice of Allowance Data Verification Completed, Apr. 20, 2004.
U.S. Appl. No. 09/069,628, Kearney, filed Apr. 29, 1998, BPAI Decision—Examiner Reversed, Jan. 20, 2004.
U.S. Appl. No. 09/069,628, Kearney, filed Apr. 29, 1998, Examiner's Answer to Appeal Brief, Sep. 25, 2001.
U.S. Appl. No. 09/069,628, Kearney, filed Apr. 29, 1998, Appeal Brief Filed, Feb. 1, 2001.
U.S. Appl. No. 09/069,628, Kearney, filed Apr. 29, 1998, Advisory Action (PTOL-303), Sep. 7, 2000.
U.S. Appl. No. 09/069,628, Kearney, filed Apr. 29, 1998, Amendment after Final Rejection, Aug. 2, 2000.
U.S. Appl. No. 09/069,628, Kearney, filed Apr. 29, 1998, Final Rejection, May 2, 2000.
U.S. Appl. No. 09/069,628, Kearney, filed Apr. 29, 1998, Response after Non-Final Action Filed, Feb. 23, 2000.
U.S. Appl. No. 09/069,628, Kearney, filed Apr. 29, 1998, Non-Final Rejection, Nov. 23, 1999.
U.S. Appl. No. 09/069,628, Kearney, filed Apr. 29, 1998, Appeal Brief, Oct. 18, 1999.
U.S. Appl. No. 09/069,628, Kearney, filed Apr. 29, 1998, Advisory Action, (PTOL-303), Aug. 4, 1999.
U.S. Appl. No. 09/069,628, Kearney, filed Apr. 29, 1998, Amendment after Final Rejection, Jul. 19, 1999.
U.S. Appl. No. 09/069,628, Kearney, filed Apr. 29, 1998, Final Rejection, Jun. 7, 1999.
U.S. Appl. No. 09/069,628, Kearney, filed Apr. 29, 1998, Supplemental Response, May 17, 1999.
U.S. Appl. No. 09/069,628, Kearney, filed Apr. 29, 1998, Response after Non-Final Action, Apr. 22, 1999.
U.S. Appl. No. 09/069,628, Kearney, filed Apr. 29, 1998, Non-Final Rejection, Feb. 16, 1999.
U.S. Appl. No. 11/171,518, Kearney, filed Jul. 1, 2005, Amendment/ Req. Reconsideration-After Non-Final Reject, Feb. 17, 2009.
U.S. Appl. No. 11/171,518, Kearney, filed Jul. 1, 2005, Non-Final Rejection, Oct. 15, 2008.
U.S. Appl. No. 11/171,518, Kearney, filed Jul. 1, 2005, Notice to the applicant regarding a non-compliant or non-responsive amendment, May 20, 2008.
U.S. Appl. No. 11/171,518, Kearney, filed Jul. 1, 2005, Response to Election / Restriction Filed, Jan. 28, 2008.
U.S. Appl. No. 11/171,518, Kearney, filed Jul. 1, 2005, Requirement for Restriction/Election, Sep. 18, 2007.
U.S. Appl. No. 11/171,518, Kearney, filed Jul. 1, 2005, Applicant Response to Pre-Exam Formalities Notice, Nov. 14, 2005.
U.S. Appl. No. 11/171,518, Kearney, filed Jul. 1, 2005, Preliminary Amendment, Nov. 14, 2005.
U.S. Appl. No. 11/216,002, Turnbough, filed Sep. 1, 2005, Abandonment, Nov. 28, 2008.
U.S. Appl. No. 11/216,002, Turnbough, filed Sep. 1, 2005, Non-Final Rejection, Apr. 14, 2008.
U.S. Appl. No. 11/216,002, Turnbough, filed Sep. 1, 2005, Response to Election / Restriction Filed, Jan. 10, 2008.
U.S. Appl. No. 11/216,002, Turnbough, filed Sep. 1, 2005, Requirement for Restriction/Election, Oct. 10, 2007.
U.S. Appl. No. 11/216,002, Turnbough, filed Sep. 1, 2005, Preliminary Amendment, Jan. 30, 2006.

* cited by examiner

**Most antibodies react specifically with spores of *Bacillus subtilis***

*B. subtilis*

*B. thuringiensis*

C11 like most — G6 — F11 and other two

```
g07    1  GGLVQPGGSRKLSCAASGFTFSSFGMHWVRQAPEKGLEWVAYISSGSSTIYYADTVKGRF
g04    1  GGLVQPGGSRKLSCAASGFTFSSFGMHWVRQAPEKGLEWVAYISSGSSTIYYADTVKGRF
g06    1  GGLVQPGGSRKLSCAASGFTFSSFGMHWVRQAPEKGLEWVAYISSGSSTIYYADTVKGRF
d06    1  GGLVQPGGSRKLSCAASGFTFSSFGMHWVRQAPEKGLEWVAYISSGSSTIYYADTVKGRF
a07    1  GGLVQPGGSRKLSCAASGFTFSSFGMHWVRQAPEKGLEWVAYISSGSSTIYYADTVKGRF
e11    1  GGLVQPGGSRKLSCAASGFTFSSFGMHWVRQAPEKGLEWVAYISSGSSTIYYADTVKGRF
a05    1  GGLVQPGGSRKLSCAASGFTFSFGMHWVRQAPEKGLEWVAYISSGSSTIYYADTVKGRF
e07    1  GGLVQPGGSRKLSCAASGFTFSSFGMHWVRQAPEKGLEWVAYISSGSSTIYYADTVKGRF
d12    1  GGLVQPGGSRKLSCAASGFTFSSFGMHWVRQAPEKGLEWVAYISSGSSTIYYADTVKGRF
d04    1  GGLVQPGGSRKLSCAASGFTFSFGMHWVRQAPEKGLEWVAYISSGSSTIYYADTVKGRF
f10    1  GGLVQPGGSRKLSCAASGFTFSFGMHWVRQAPEKGLEWVAYISSGSSTIYYADTVKGRF g07   61  TISRDNPKNTLFLQMTSLRSEDTVMYYCAR....RGTGTRYFDYWGQGXTSTVSSEQSF
g04   61  TISRDNPKNTLFLQMTSLRSEDTAMYYCAT....YRIYS..MDYWGQGTVTVSSEQF
g06   61  TISRDNPKNTLFLQMTSLRSEDTAMYYCARSGHDYGYSRGYFDVWGAGTTVTVSSEQF
d06   61  TISRDNPKNTLFLQMTSLRSEDTAMYYCARSGHYYGYSRGYFDVWGAGTTVTVSSATTTA
a07   61  TISRDNPKNTLFLQMTSLRSEDTAMYYCA....WEVSTRYFDVWGAGTTVTVSSATTTA
e11   61  TISRDNPKNTLFLQMTSLRSEDTAMYYCARYDT..TVVSRAMDYWGQGTVTVSSATTTA
a05   61  TISRDNPKNTLFLQMTSLTSEDTAMYYCARRNC..G.SRRAIDYWGQGTVTVSSATTTA
e07   61  TISRDNPKNTLFLQMTNLRSEDTAMYYCARW.....DSLRTFAYWGQGTLVTVSSAKTTA
d12   61  TISRDNPKNTLFLQMTSLRSEDTAMYYCARW......LLRAMDYWGQGTVTVSSAKTTA
d04   61  TISRDNPKNTLFLQMTSLRSEDTAMYYCARHYYGTNYVRAMDYWGQGTVTVSSAKTTA
f10   61  TISRDNPKNTLFLQMTSLRSEDTAMYYCARHYYDEGPHWYFDVWGAGTTVTVSSAKTT g07  117  PNVSPLVSCESPLSDKNLVSGCLDPD~ (SEQ ID NO:7)
g04  115  PNVSPLVSCESPLSDKNLVSGCLAED~ (SEQ ID NO:8)
g06  121  SNVSPLVSCESPLSDKNLVSGCLDPD~ (SEQ ID NO:9)
d06  121  PSVYPLVPGCIDTSGSS.VTLGCLVKAT (SEQ ID NO:10)
a07  117  PSVYPLVPGCSDTSGSS.VTLGCLVKAT (SEQ ID NO:11)
e11  119  PSVYPLVPGCIDTSGSS.VTLGCLVKAT (SEQ ID NO:12)
a05  118  PSVYPLVPGCSDTSGSS.VTLGCLVKAT (SEQ ID NO:13)
e07  116  PSVYPLAPVCGDTSGSS.VTLGCLVKGY (SEQ ID NO:14)
d12  115  PSVYPLAPVCGDTSGSS.VTLRCLVKGY (SEQ ID NO:15)
d04  121  PSVYPLAPGCGDTSGSS.STLGCLVNGY (SEQ ID NO:16)
f10  121  PSVYPLAPGCGDTSGSS.VTLGCLVKGY (SEQ ID NO:17)
```

Fig 4

Ab-derived Peptides Specifically Bind Bacillus subtilis Spores

Framework 3
VH7183
consensus

VH7183-6

B. subtilis    B. thuringiensis    B. anthracis

VH7183-6            RFTISRDNPKNTLFLQMT
VH7183 consensus    RFTISRDNAKNTLYLQMS

**Anti-*Bacillus anthracis* Ab Specifically Bind *Bacillus anthracis* Spores**

*B. anthracis*     *B. subtilis*     *B. thuringiensis*

```
2     1  ------------------------------------------
3     1  ------------------------------------------
4     1  ------------------------------------------
9-1   1  ----PSQSLSLTCSVSGFSLSGYGVHWVRQRPGKGLECLGMLWGVG...
7-1   1  ------------------FTFSNYYMSWVRQPPGKSLEWVGFIINKANG
24-2  1  -GGLVKPGGSLKLSCAASGFTFSSYAMSWVRQTPEKRLEWVATISSGG...
21-4  1  -GGLVKPNGSLKLSCAASGFTFSSYAMSWVRQTPEKRLEWVATISSGG...
10-2  1  -GGLVKPWRSLKLSCAASGFTFSSYAMPWVRQTPEKRLEWVATIRSGG...
22-1  1  -GHLVKPGGSLKLSCAASGFTFSSYAMSWVRQTPDKRLEWVATISSGG...
13-3  1  -NELARPGPSVKMSCKASGYTFTRYAMHWVKQRPGQGLEWIGYINPSS...
8-3   1  GAELVRPGTSVKVSCKASGYTFTNYWIGWVRQRPGHGLEWMGDIYPGG...
6-1   1  ----ELGKSVKLSCKASGYTFSSYWMHWVLLRHGQGLEWIGNIYPGS...
3-1   1  GNELAKPGASVKMSCKASGYTFSSYWMHWVKQRPGQGLEWIGYINPSP...
1     1  ------------------------------------------

2     1  ------------------------------------------
3     1  ------------------------------------------
4     1  ------------------------------------------
9-1   43 .SPDYNSARKSRLSISRDNSKSQVFLKMNSLQAEDTAMYYCARDYYGNYV
7-1   32 YTTEYSASVKGRFTISRDNSQSILYLQMNSLRAEDSATYYCARAYYGNYP
24-2  48 SYTYYPDSVKGRFTISRDNAKNTLYLQMSSLRSEDTAMYYCARQGLRR..
21-4  48 SYTYYPDSVKGRFTISIDNAKNTLYLQMSSLRSEDTAMYYCARQGLRR..
10-2  48 SYTYYPDSVKGRFTISRDNAKNTLYLQMSSLRSEDTAMYYCPIYD..G..
22-1  48 SYTYYPDSVKGRFTISRDNEKNTLYLQMSSLRSEDTAMYYCARAGITTAI
13-3  48 GYTNYNQKFKDKATLTADKSSRTAYMQLSSLTSEDSAVYYC...RVTAR
8-3   49 GYTNYNEKFKGKATLTADTSSSTAYMQLSSLTSEDSAIYYC...RGNLG
6-1   44 GSTNYDEKFRDKGTFVDTSSSTAYHELSSLTSEDSAVYYCQRKGRGSGY
3-1   49 GYTEYNQKFKDKATLTADKSSSTAYMQLSSLTSEDSAIYYCARIGSGYVG
1     1  ------------------------------------------

2     1  ----------------TYPLPIR-------------------  (SEQ ID NO:18)
3     1  ----------------TYPPFR--------------------  (SEQ ID NO:19)
4     1  ----------------TYPPHR--------------------  (SEQ ID NO:20)
9-1   92 WYFDVWGAGTAVTVSSAKTTPPSVYPLAPGCGDTTGSS.VTLGCLVKGY  (SEQ ID NO:21)
7-1   82 AWFAYWGQGTLVTVSFAKTTAPSVYQLAPVCGDTTGSS.VTLGCLVKGY  (SEQ ID NO:22)
24-2  96 YAMDYWGQGTSVTVSSAKTTPPSVYPLAPGFGDTTGSS.VTLGCLVKGY  (SEQ ID NO:23)
21-4  96 VAMDYWGQGTSVTVSSAKTTAPSVYQLAPGTGDTTGSS.VTLGCLVKG~  (SEQ ID NO:24)
10-2  94 HAMDYWGQGTSVTVSSATTTAPSVYPLVPGCDTTGSS.VTLGCLVKGY  (SEQ ID NO:25)
22-1  98 YAMDYWGQGTSVTVSSESQSFPNVEPLVSCESPLEDKNLVAMGCLARD-  (SEQ ID NO:26)
13-3  95 YAMDYWGQGTSVTVSSAKTTPSVYPLAPVCGDTTGSS.VTLGCLVKGY  (SEQ ID NO:27)
8-3   96 ...DYWGQGTSTVTVSSAKTTAPSVYPLAPVCGDTTGSS.VTLGCLVKGY  (SEQ ID NO:28)
6-1   94 DEMDYWGQGTSVTVSSAKTTAPSVYPLAPVCGDTTGSS.VTLGCLVKGY  (SEQ ID NO:29)
3-1   99 YAMDYWGQGTSVTVSSESQSFPNVEPLVSCESPLEKNLVAMGCLARD~  (SEQ ID NO:30)
1     1  ---------TSQNVRS--------------------------  (SEQ ID NO:31)
```

Fig 7

MONOCLONAL ANTIBODIES SPECIFIC FOR ANTHRAX SPORES AND PEPTIDES DERIVED FROM THE ANTIBODIES THEREOF

CROSS-REFERENCE TO RELATED APPLICATIONS

The present application is a continuation of, and claims priority to, U.S. application Ser. No. 11/171,518, filed Jul. 1, 2005 now abandoned, which is a continuation of and claims priority to U.S. application Ser. No. 09/069,628, now U.S. Pat. No. 6,913,756, filed Apr. 29, 1998, which applications are incorporated herein by reference in their entirety.

STATEMENT REGARDING FEDERALLY SPONSORED RESEARCH OR DEVELOPMENT

This invention was made with government support under GM 054068 awarded by the National Institutes of Health. The government has certain rights in the invention.

BACKGROUND OF THE INVENTION

1. Field of the Invention

The present invention relates generally to the fields of immunology and microbiology. More specifically, the present invention relates to monoclonal antibodies specific for anthrax spores and peptides derived from the antibodies.

2. Description of the Related Art

During the evolution of the immune system there is evidence that the repertoire of germline V genes that has been retained in the genome has been subject to selective processes by environmental influences which may include self as well as commensal and non-commensal microorganisms. Structural and functional analysis of immunoglobulin and T cell receptors have delineated regions of these molecules which are germline encoded and have the ability to bind to certain bacterial components through exposed parts of the molecules which do not need somatic diversification for expression of the ability to bind to these structures. Some of these included protein A binding to framework three (FR3) region of $V_H$ genes, staphylococcal enterotoxin binding to T cell receptor, etc.

The prior art is deficient in the lack of monoclonal antibodies which are highly specific and can discriminate between spores of the *Bacillus* family including the strategically important *B. anthracis*. Further, the prior art is deficient in the lack of peptides derived from the monoclonal antibodies highly specific for *Bacillus* spores. The present invention fulfills this longstanding need and desire in the art.

SUMMARY OF THE INVENTION

The present invention is directed to monoclonal antibodies which are highly specific for anthrax spores and peptides derived from the antibodies. The present invention demonstrated that the humoral immune response to spores of *Bacillus* show a remarkable conservation of $V_H$ gene usage which is distinct for each spore analyzed. The results imply evolutionary conservation of $V_H$ genes due to their ability to bind spores. Furthermore, of highly practical importance, these antibodies can discriminate between spores of potentially lethal organisms such as *B. anthracis* and other harmless but closely related *bacilli* and provide a very powerful tool in the construction of detection instruments as counter measures in biological warfare.

In one embodiment of the present invention, there is provided a monoclonal antibody specific for *Bacillus* spores. Preferably, *Bacillus* is selected from the group consisting of *Bacillus anthracis, Bacillus thuringiensis, Bacillus subtilis* and other *bacilli* related to *Bacillus anthracis*. Preferably, the antibody is IgG.

In another embodiment of the present invention, there is provided a peptide derived from the monoclonal antibody highly specific for *Bacillus* spores.

In yet another embodiment of the present invention, there is provided a method of preparing the monoclonal antibody highly specific for *Bacillus* spores by immunizing and fusing local lymph nodes of an animal.

In still yet another embodiment of the present invention, there is provided a method of detecting *Bacillus* spores in a field sample using a monoclonal antibody highly specific for the *Bacillus* spores by contacting the sample with a monoclonal antibody disclosed herein.

In still yet another embodiment of the present invention, there is provided a method of detecting *Bacillus* spores in a field sample using a peptide derived from a monoclonal antibody highly specific for the *Bacillus* spores by contacting the sample with a peptide derived from a monoclonal antibody highly specific for *Bacillus* spores.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2 shows that anti-spore monoclonal antibodies do not react with vegetative bacteria.

FIG. 3 shows that most antibodies react specifically with spores of *Bacillus subtilis*.

FIG. 4 shows that a commonly used member $V_H7183.6$ heavy chain gene of the $V_H7183$ (MOPC21) family in all hybridomas reactive with *Bacillus subtilis* spores appears to be the most unique member of this family in the framework three (FR3) region. (Hybridomas g07 to f10 are labeled SEQ ID NO: 7 to SEQ ID NO: 17, respectively)

FIG. 5 shows that antibody-derived peptides specifically bind *Bacillus subtilis* spores.

FIG. 6 shows that anti-*Bacillus anthracis* antibody specifically bind *Bacillus anthracis* spores.

FIG. 7 shows that the $V_H$ gene sequences among monoclonal antibodies to *Bacillus anthracis*. (SEQ ID NO: 18 to SEQ ID NO: 31)

DETAILED DESCRIPTION OF THE INVENTION

Figure 1:
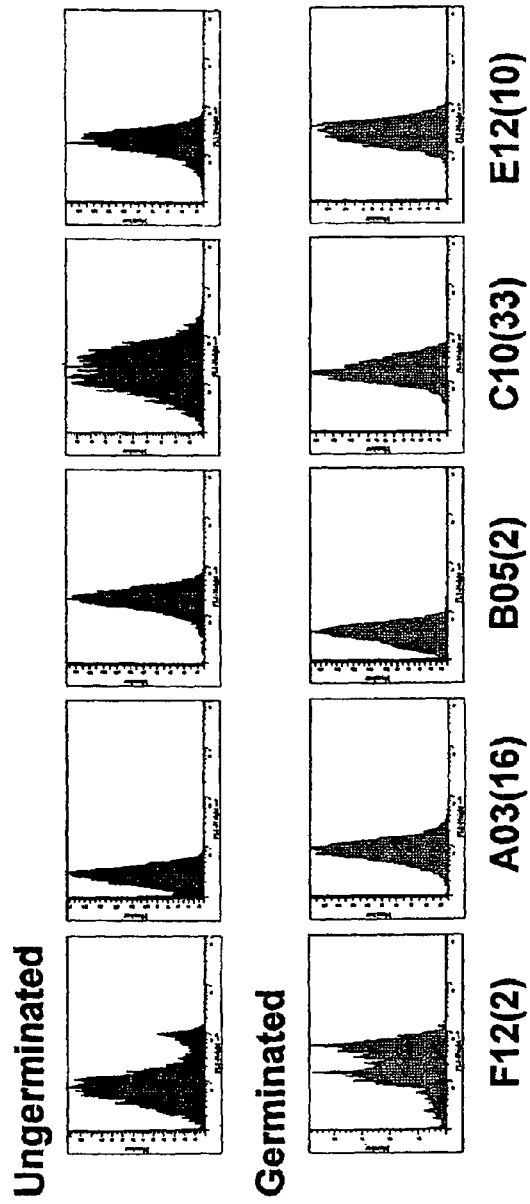
FIG. 1 shows antibodies with different reactivities for germinated and ungerminated spores among different clones.

In the present invention, panels of monoclonal antibodies which are highly specific and can discriminate between spores of the *Bacillus* family including the strategically important *Bacillus anthracis* (anthrax) were isolated and characterized. The amino acid sequences of these anti-spore antibodies were determined from the nucleotide sequences of the coding genes and smaller peptide molecules were derived from these antibodies which can also bind *Bacillus* spores.

The present invention is directed to a monoclonal antibody highly specific for *Bacillus* spores. Preferably, *Bacillus* is selected from the group consisting of *Bacillus anthracis*, *Bacillus thuringiensis*, *Bacillus subtilis* and other *bacilli* closely related to *Bacillus anthracis*. Preferably, the antibody is IgG. The present invention is also directed to a peptide derived from the monoclonal antibody highly specific for *Bacillus* spores. Preferably, the peptide can also bind the *Bacillus* spores specifically.

Also disclosed in the present invention is a method of preparing a monoclonal antibody highly specific for *Bacillus* spores, comprising the steps of immunizing an animal with the *Bacillus* spores and fusing local lymph nodes of the animal.

The present invention also is directed to a method of detecting anthrax in a field sample using a monoclonal antibody highly specific for *Bacillus anthracis* spores by contacting the sample with the monoclonal antibody and measuring the amount of binding of the antibody to the sample compared to an appropriate control.

The present invention also is directed to a method of detecting lethal *Bacillus* spores in a field sample using the peptide derived from the monoclonal antibody highly specific for *Bacillus* spores by contacting the sample with the peptide and measuring the amount of binding of the peptide to the sample compared to an appropriate control.

The following terms have the definitions set below.

As used herein, "hybridoma" refers to a continuously growing antibody-secreting cell line derived from the fusion of a specific normal antibody-forming B cell from an immunized mouse with an immortal myeloma cell line. Hybridomas secrete monoclonal antibodies described herein.

As used herein, "homogeneous staining" refers to the uniform staining at a similar intensity of all spores in a given sample.

As used herein, "heterogeneous staining" refers to the staining of one or more populations of spores in a given sample.

As used herein, "unfixed untreated spores" refers to spores that are in their native state in water and not treated with any kind of fixation reagent such as formalin or glutaraldehyde or paraformaldehyde.

As used herein, "two-color flow cytometric analysis" refers to the identification of spore subpopulations or other particles by fluorescence activated flow cytometry using two independent fluorochrome labeled antibodies.

As used herein, "limiting dilution" refers to the distributing of hybridoma cells into tissue culture plates such that less than 30% of the wells contain a growing clone. Each well, according to the Poisson distribution, should contain the progeny of only one cell.

The following examples are given for the purpose of illustrating various embodiments of the invention and are not meant to limit the present invention in any fashion.

Example 1

Animals

Eight to twelve-week-old BALB/c mice were purchased from Charles River Laboratories (Raleigh, N.C.) or bred in our mouse facility. BALB/c mice were used for immunization and obtaining feeder cells for subcloning of hybridomas, phenotypic analysis and functional studies. Mice were housed in accordance with institutional policies for animal care and usage.

Example 2

Bacterial Spores

*B. subtilis* spores were provided by Dr. Chuck Turnbough. *B. anthracis* spores were obtained from Dr. Joany J. Jackman at USAMIRID and *B. thuringiensis* spores were obtained from Abbott Laboratories.

Example 3

Antibody Production: Immunization and Fusion

Six-week-old female BALB/c mice were inoculated with $5 \times 10^8$ spores emulsified in complete Freund's adjuvant at day 0, and then repeatedly with spores in saline at days 3, 6, 9, 13, 17 and 20 in subcutaneous sites in the rear legs and inguinal regions.

On day 21, popliteal, inguinal and iliac lymph nodes draining sites of injection were removed, a lymphocyte suspension was prepared and fused to P3×63Ag8.653 using a modification of the method described by Kohler and Milstein. Fused cells were plated on ten 96-well plates in DMEM supplemented with 20% fetal bovine serum (FBS), 2 mmol/L L-glutamine, HAT medium, and FCS (from HyClone Laboratories Inc., Logan, Utah; other reagents from Sigma), and placed in a 37° C. incubator with 9% $CO_2$.

Example 4

Primary Screening and Subcloning

Hybridoma supernatants were screened on spore suspensions using two-color flow cytometric analysis. Binding of secreted mouse Ig from supernatants to the spores was traced with Phycoerythrin (PE)-conjugated goat anti-mouse Ig (Southern Biotechnology Associates, Birmingham, Ala.). Data from stained cell samples were acquired using a FACScan™ or FACSCalibur™ flow cytometer with lysis II and Cell Quest software packages (Becton Dickinson, Mountain View, Calif.) and analyzed with WinList 2.01 (Verity Software House, Inc.) and WinMDI 2.0 software programs (Trotter@scripps.edu).

Example 5

ELISA

Flat bottom ELISA plates (E.I.A.A/2 plates, Costar) were coated with poly-L-Lysine (50 µg) for 30 minutes and a suspension of spores at $2 \times 10^8$/ml (40 µl) in distilled water were allowed to dry on the plates overnight. Supernatants were added and after incubation developed with goat anti-mouse Ig. Between each step, the plate was washed five times with PBS. The plate was developed with alkaline phosphatase substrate (Sigma, St. Louis, Mo.) (1 mg/ml) in substrate buffer (pH 9). For quantitative ELISA, mouse antibody of known concentration was used as a standard in each plate and $OD_{405}$ values of plates were read by a Titertek Multiskan Plus MKII™ spectrophotometer (Flow, McLean, Va.). Antibody concentration was determined using an ELISALITE™ program (Meddata, New York, N.Y.).

Example 6

Antibody Purification and Conjugation

Pure anti-spore antibodies were prepared from bulk hybridoma cultures by protein G chromatography. FITC and phycoerythrin conjugates were prepared using standard procedures.

Example 7

Immunofluorescence and Immunohistochemical Analysis of Tissue Sections and Cytocentrifuge Preparations Spleens embedded in OCT™ compound (Lab-Tek Products, Naperville, Ill.) were flash frozen in liquid nitrogen. Frozen sections were cut, air dried, fixed in ice-cold acetone, blocked with normal horse serum, and macrophages stained with MOMA-1 (rat, IgG2a, 10 μg/ml, from Dr. Georg Kraal), each developed with biotin-conjugated goat anti-rat IgG (SBA). Next, the sections were blocked with normal rat serum followed by anti-spore reagents and secondary reagents and streptavidin AMCA (Vector Laboratories, Burlingame, Calif.). Spore suspension in distilled water were dryed onto poly-L-Lysine treated glass slides for 2 hours at 37° C., blocked with 1% BSA and PBS and stained with antibodies for microscopy of spore suspensions.

Tissue sections and slides with dried spores were washed and mounted in Fluormount G™ (SBA, Birmingham, Ala.) and viewed with a Leica/Leitz DMRB fluorescence microscope equipped with appropriate filter cubes (Chromatechnology, Battleboro, Vt.). Images were acquired with a C5810 series digital color camera (Hamamatsu Photonic System, Bridgewater, N.J.) and processed with Adobe PhotoShop™ and IP LAB™ Spectrum software (Signal Analytics Software, Vienna, Va.).

Example 8

DNA Sequencing Analysis $V_H$ and $V_K$ gene sequencing was carried out from cDNA isolated from hybridomas. To make cDNA, total RNA was isolated from hybridomas using guanidinium thiocyanate-phenol-chloroform extraction. The cDNA was synthesized using an oligo-dT primer followed by PCR using a Cμ 3' primer (SEQ ID NO: 1) and $V_H$7183-specific primer (SEQ ID NO: 2) for the heavy chains or a $C_K$ 3' primer (SEQ ID NO: 3) and a degenerate $V_K$ 5' primer (SEQ ID NO: 4) for the light chains. The PCR amplified DNA was cloned into Bluescript II KS™ and subjected to sequencing using a Sequenase™ Kit (Strategene, La Jolla, Calif.). The DNA sequences were analyzed using the DNAstar™ program.

Example 9

Antibodies to B. subtilis

Two immunization were made, one with fixed spores which gave only 3/192 (1.6%) monoclonal antibodies (mAbs) reactive with spores; and the other with unfixed spores which gave 95/384 (25%) (mAbs) reactive with spores, another 89 (20%) weakly reactive. These 576 clones were then tested against other spore components and 15 reacted with NAD synthetase, 6 with RNA polymerase, 5 with cot TC, 2 with SSPC, and 1 with cse60 by ELISA. Totally, 136 clones were reactive with spores or purified/recombinant components.

Among the clones reactive with the intact spores, certain patterns were observed: (1) two clones appeared to dramatically alter the FSC/SSC profile of spores on flow cytometry; (2) some clones reacted with germinated, but not with ungerminated spores; and (3) the majority had homogenous staining of germinated, but heterogeneous staining of ungerminated spores (FIG. 1).

Figure 2:
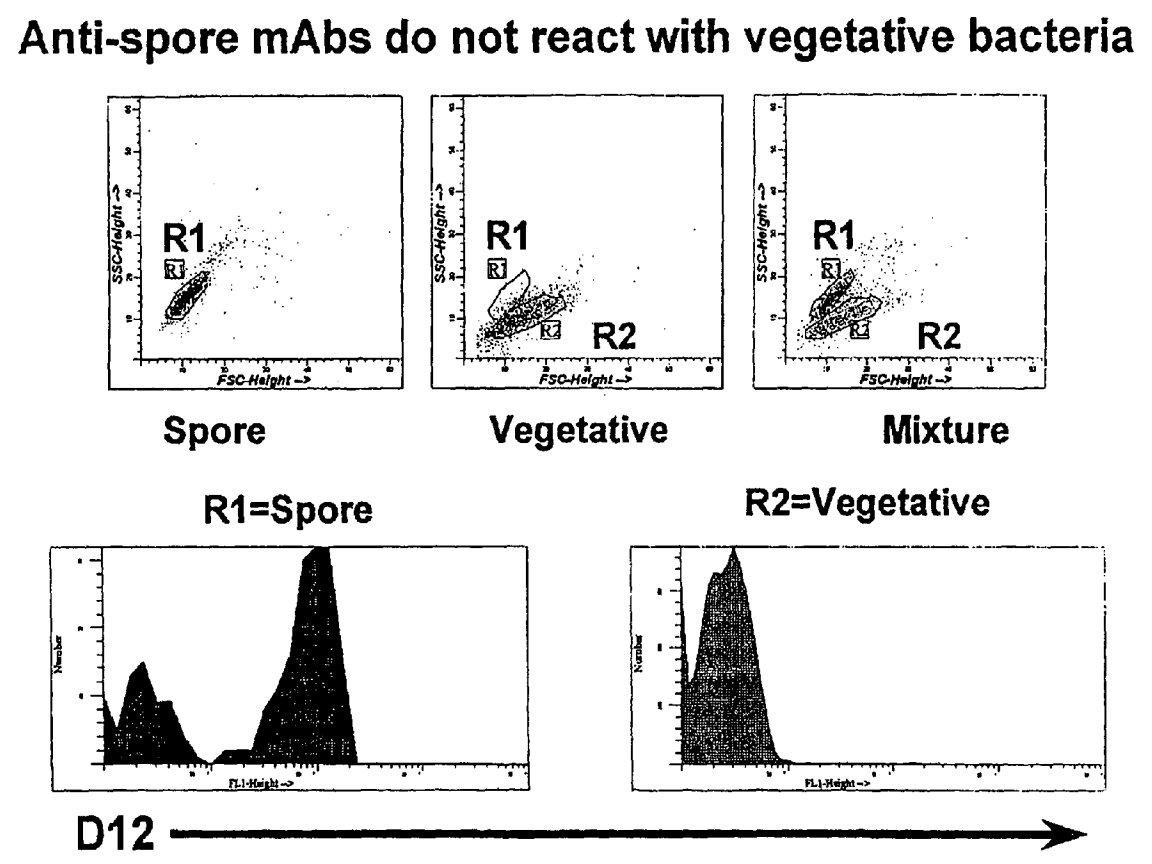

96 clones of hybridomas reactive with B. subtilis were picked up and grown on a new plate. They include two negative clones, the clones reactive with purified proteins or peptides and clones reactive with spores representing different patterns. These antibodies were tested on the vegetative forms of B. subtilis (i.e., live bacteria) and were found to be negative (FIG. 2). They also did not react with two other species of spore-forming Bacilli (FIG. 3). Isotyping of the antibodies produced by these clones revealed that many (55/96) use λ light chains. Additionally, it was also unusual that 4 of these antibodies use α heavy chains.

All 96 clones were subcloned by limiting dilution and tested by flow cytometry. 68/96 were still reactive with spores and all except one were monoclonal. The reactive clones can be basically separated into two groups: those reactive with all spores and the other reactive with subsets of spores. Since these antibodies are of different isotypes, multiple parametric flow cytometric analysis could be done next. These important results showed that fixation of spores did not permit production of antibodies to the intact native spores and it was only when unfixed untreated spores were used to immunize mice could many highly specific antibodies to B. subtilis be isolated.

Example 10

Sequence Analysis of Monoclonal Antibody to B. subtilis

The striking over usage of λ light chains in the antibodies led to sequencing the heavy and light chains of the genes from hybridomas synthesizing the B. subtilis spore specific antibodies to obtain an idea of the heterogeneity of antibodies generated. The heavy chains revealed remarkable homogeneity of $V_H$ gene usage in that all hybridomas used a member of $V_H$7183 (MOPC21) family.

This member $V_H$7183.6 appears to be the most unique member of this family in the framework three (FR3) region as shown in FIG. 4. The CDR3 region was diverse in nearly all cases and used variable $D_H$ and $J_H$ genes. These results suggest that there is a very strong selection for the use of this $V_H$ gene despite the similarities inherent in the family members of this family. λ light chain sequence showed the exclusive use of Vλ1 Cλ1 with different CDR3 regions. Six of these were selected for further study and characterization.

Example 11

Isolation of FR3 Peptides Which Bind to Spores

Based on the sequences of VH genes utilized in antibodies against *Bacillus subtilis* spores, two peptides were designed: one corresponding to the consensus sequence of these antibodies in the framework 3 region (Peptide Anti-spore: SEQ ID NO: 5), and the other corresponding to the consensus sequences of the 7183 $V_H$ gene family to which the particular $V_H$ gene belongs (Peptide 7183 consensus: SEQ ID NO: 6).

The carboxyl-terminal cysteine was added for fluorochrome conjugation. Both peptides were conjugated with phycoerythrin, and tested for their ability to bind *Bacillus subtilis* spores. 7183 consensus peptide was designed to be a control. It was found that the peptides derived from the anti-spore antibody stained brightly at 2 µg/ml (1 µM), while the consensus peptide stained spores at 200 µg/ml (100 µM) (FIG. 5). Thus the peptide derived from the spore specific nucleotide derived antibody sequence bind strongly and specifically to *B. subtilis*.

Example 12

Serum Antibody Response to *B. subtilis* Spore Immunization

The immune response to *Bacillus subtilis* spores was characterized in mice. BALB/c mice were immunized with either spores or PBS (control). The mice were bled at 1, 2 and 3 weeks after immunization. Serum antibodies of different isotypes specific for spores were quantitated using ELISA. It was found that (1) immune responses peaked at 1 week; (2) light chain-containing antibodies account for about 30% of total spore-specific immunoglobulins; and (3) in contrast to all other isotypes, IgG3 antibodies continue to increase over the 3-week period. These findings confirmed the hybridoma analysis that the immune response to *B. subtilis* spores is dominated by a particular set of B cell clones.

Example 13

Monoclonal Antibodies to *B. anthracis*

Mice were immunized with a 50:50 mix of heavily irradiated ($4 \times 10^6$ Gy) *Bacillus anthracis* spores of the Ames and Sterne strains, generated hybridomas, and screened for antibody production by FACS analysis. About 60 hybridomas were selected for further characterization. A similar pattern of reactive antibodies was obtained with some of these panels binding 100% of *B. anthracis* spores. A seen in FIG. 6, a representative profile of more than 36 anti-anthrax antibodies which stain all spores but were not at all reactive with *B. subtilis* and *B. thuringiensis* spores. The $V_H$ gene sequences were determined and are shown in FIG. 7. Again a similar conservation in $V_H$ usage was found similar to what was found in antibodies to *B. subtilis*. In this case, one of the two $V_H$ genes is from $V_H7183$ and the other from the $V_HJ558$ family predominates. A third $V_H$ gene is from the $V_H$ Q52 family.

Example 14

Monoclonal Antibodies to *B. thuringiensis*

Figure 8:
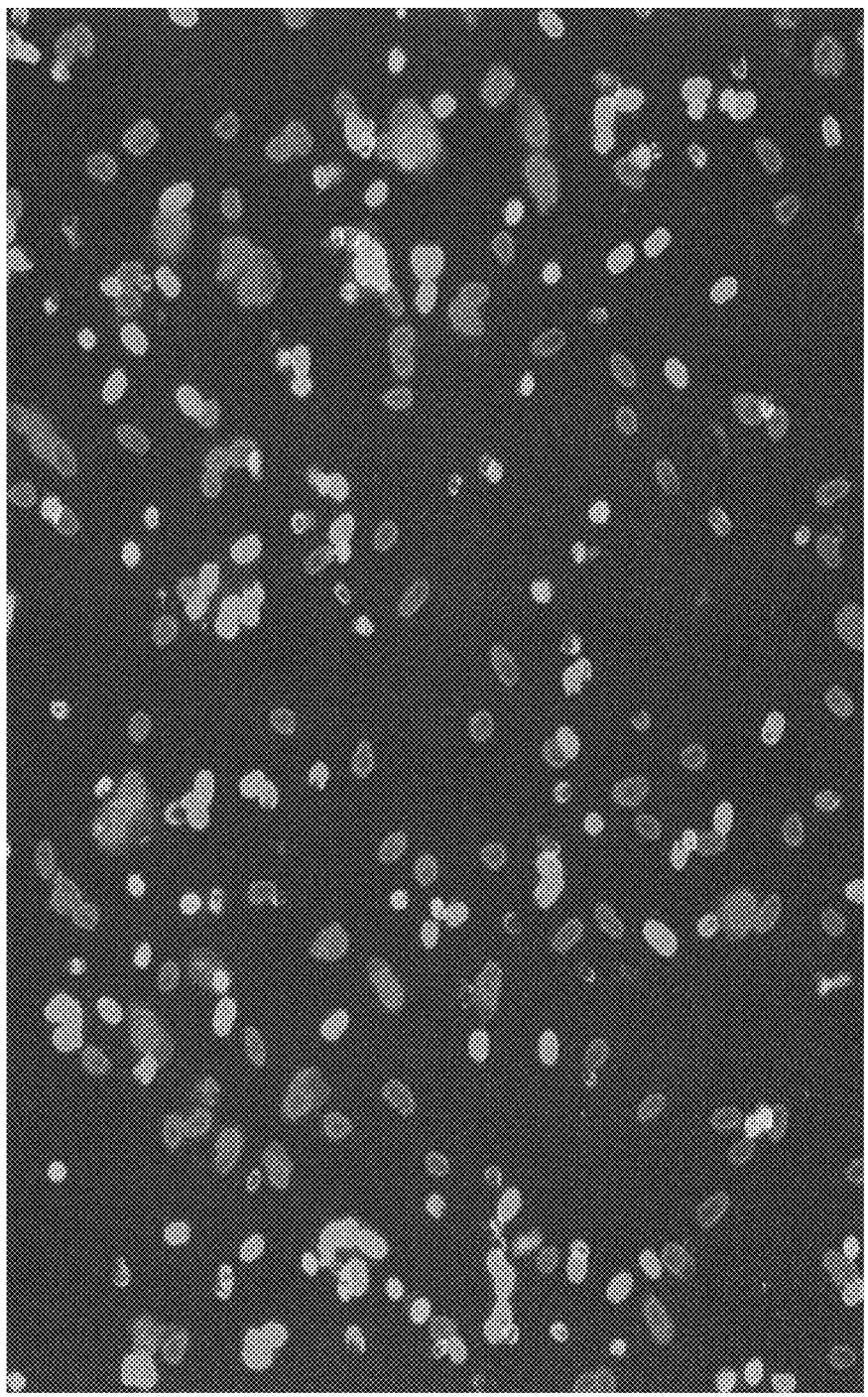
FIG. 8 shows the discriminatory ability of the antibodies in vitro. *Bacillus anthracis, Bacillus subtilis* and *Bacillus thuringiensis* spores were mixed and stained on a slide with fluorescent antibodies labeled with blue, green and red antibodies, respectively.
Figure 9:
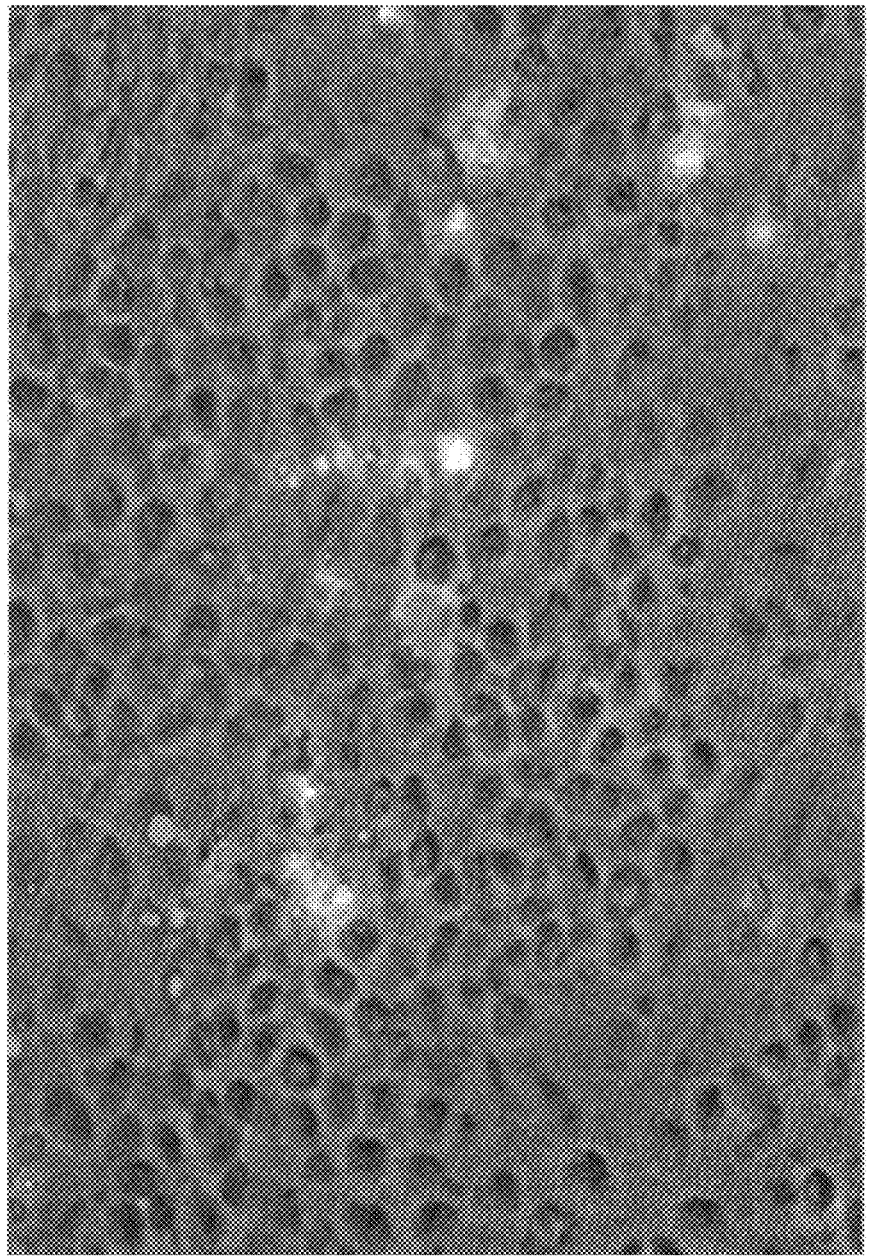
FIG. 9 shows the discriminatory ability of the antibodies in vivo. A section of mouse spleen was injected 30 minutes previously with *Bacillus anthracis*, *Bacillus thuringiensis*, *Bacillus subtilis* spores and labeled with blue, green and red antibodies, respectively.

A similar strategy was used to isolate and characterize ~100 antibody forming hybridomas which reacted with *B. thuringiensis*. Again the pattern was similar with all reacting with *B. thuringiensis* but not *B. subtilis* or *B. anthracis*. These antibodies were cloned and are sequenced. The discriminatory ability of antibodies is shown in FIGS. 8 and 9 where it is possible to clearly discriminate three distinct spore staining by fluorescence in a mixture of the three kinds of spores in vitro and in vivo.

Example 15

Discussion

The work presented here disclosed panels of antibodies which are highly specific and can discriminate between spores of the *Bacillus* family including the strategically important *B. anthracis* (anthrax). This is the first time such antibodies have been isolated and characterized. The reagents used in the various Divisions of the Armed services for testing were not monoclonal. They were made in sheep and other species against *B. subtilis* and *B. anthracis*.

The antibodies disclosed in the present invention are unique because of several reasons: (1) the spores were not fixed with glutaraldehyde or formalin (which chemically modifies the spores) before immunization; (2) these are monoclonal antibodies made by immunizing and fusing local lymph nodes. Such a procedure has not been used in the past. The few monoclonal antibodies described before have been of the IgM isotypes which are more difficult antibodies to use and are more cross-reactive, i.e., react with spores other than *B. anthracis*, while the monoclonal antibodies disclosed herein are IgG. IgM antibodies of this kind are useless in instruments designed to give positive results for anthrax spores in the field, since such antibodies will also detect harmless spores such as *B. subtilis* which is ubiquitous in the environment.

The amino acid sequences of these anti-spore antibodies were also analyzed, which allows one to design and make smaller peptide molecules which can also bind spores. These will be more rugged molecules than the large antibody molecule and can be used in other kinds of detectors. Such peptides are totally unique in their binding to *Bacillus* spores.

There are numerous government (services and intelligence), as well as private groups trying to make instruments that are small, portable and highly accurate in their detection of small numbers of potentially lethal spores such as anthrax. The monoclonal antibodies presented here could play a critical role in their instrument development program. Such findings will be significant in detecting air and water containing anthrax spores for civilian and military use.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of preparing a monoclonal IgG antibody specific for *Bacillus anthracis* spores, comprising the steps of:
   immunizing an animal with unfixed *Bacillus anthracis* spores; and
   fusing lymph nodes located at the draining site of the immunization of said animal with a myeloma cell to produce a hybridoma cell that produces a monoclonal antibody specific for *Bacillus anthracis* spores.

2. The method of claim 1, wherein said animal is a mouse.

3. A method of detecting *Bacillus anthracis* spores in a field sample using a monoclonal IgG antibody specific for said spores, comprising the steps of:
   contacting said sample with a monoclonal antibody specific for *Bacillus anthracis* spores, wherein the monoclonal antibody is prepared by a method comprising immunizing an animal with unfixed *Bacillus anthracis* spores; and
   detecting the presence of the monoclonal antibody, wherein the presence of the monoclonal antibody indicates the presence of spores.

4. The method of claim 1, wherein the unfixed spore is irradiated prior to immunizing the animal.

5. A method of detecting *Bacillus anthracis* spores in a field sample using a monoclonal antibody specific for said spores, comprising the step of:
   contacting said sample with a monoclonal antibody prepared by the method of claim 1; and
   detecting the presence of the monoclonal antibody, wherein the presence of the monoclonal antibody indicates the presence of spores.

* * * * *

SEQUENCE LISTING

<160> NUMBER OF SEQ ID NOS: 31

<210> SEQ ID NO 1
<211> LENGTH: 32
<212> TYPE: DNA
<213> ORGANISM: Artificial Sequence
<220> FEATURE:
<223> OTHER INFORMATION: Cm 3' primer used to amplify VH cDNA

<400> SEQUENCE: 1
gaagcttata cacagttggt gcagcatcag cc                                    32

<210> SEQ ID NO 2
<211> LENGTH: 32
<212> TYPE: DNA
<213> ORGANISM: Artificial Sequence
<220> FEATURE:
<223> OTHER INFORMATION: VH7183-specific primer used to amplify VH cDNA

<400> SEQUENCE: 2
cgcgcggccg cgtggagtct gggggaggct ta                                    32

<210> SEQ ID NO 3
<211> LENGTH: 30
<212> TYPE: DNA
<213> ORGANISM: Artificial Sequence
<220> FEATURE:
<221> NAME/KEY: primer_bind
<223> OTHER INFORMATION: Ck 3' primer used to amplify Vk cDNA

<400> SEQUENCE: 3
gaagcttata cagttggtgc agcatcagcc                                       30

<210> SEQ ID NO 4
<211> LENGTH: 30
<212> TYPE: DNA
<213> ORGANISM: Artificial Sequence
<220> FEATURE:
<223> OTHER INFORMATION: Vk 5' primer used to amplify Vk cDNA;
      base 9, u = pseudouridine; bases 12, n = other = q or
      queosine; bases 13 and 15, n = other = i or inosine

<400> SEQUENCE: 4
gccatggtur tnnwnmtsac ccagtctcca                                       30

<210> SEQ ID NO 5
<211> LENGTH: 19
<212> TYPE: PRT
<213> ORGANISM: Artificial Sequence
<220> FEATURE:
<223> OTHER INFORMATION: Peptide Anti-spore: artificial peptide
      corresponding to consensus sequence in the framework 3 region of
      antibodies against Bacillus subtilis spores.

<400> SEQUENCE: 5

Arg Phe Thr Ile Ser Arg Asp Asn Pro Lys Asn Thr Leu Phe Leu
                5                  10                  15

Gln Met Thr Cys

<210> SEQ ID NO 6
<211> LENGTH: 19
<212> TYPE: PRT
<213> ORGANISM: Artificial Sequence
<220> FEATURE:
<223> OTHER INFORMATION: Peptide 7183: artificial peptide corresponding
      to consensus sequence in 7183 VH gene family.

-continued

<400> SEQUENCE: 6

Arg Phe Thr Ile Ser Arg Asp Asn Ala Lys Asn Thr Leu Tyr Leu
                5                   10                  15

Gln Met Ser Cys

<210> SEQ ID NO 7
<211> LENGTH: 143
<212> TYPE: PRT
<213> ORGANISM: Mus musculus
<220> FEATURE:
<223> OTHER INFORMATION: Sequence of framework three (FR3) region in
      hybridoma g07 incorporating VH7183.6 heavy chain gene from the
      VH7183 (MOPC21) family

<400> SEQUENCE: 7

Gly Gly Leu Val Gln Pro Gly Gly Ser Arg Lys Leu Ser Cys Ala
                5                   10                  15

Ala Ser Gly Phe Thr Phe Ser Ser Phe Gly Met His Trp Val Arg
                20                  25                  30

Gln Ala Pro Glu Lys Gly Leu Glu Trp Val Ala Tyr Ile Ser Ser
                35                  40                  45

Gly Ser Ser Thr Ile Tyr Tyr Ala Asp Thr Val Lys Gly Arg Phe
                50                  55                  60

Thr Ile Ser Arg Asp Asn Pro Lys Asn Thr Leu Phe Leu Gln Met
                65                  70                  75

Thr Ser Leu Arg Ser Glu Asp Thr Val Met Tyr Tyr Cys Ala Arg
                80                  85                  90

Arg Gly Thr Gly Thr Arg Tyr Phe Asp Tyr Trp Gly Gln Gly Ala
                95                  100                 105

Thr Leu Thr Val Ser Ser Glu Ser Gln Ser Phe Pro Asn Val Phe
                110                 115                 120

Pro Leu Val Ser Cys Glu Ser Pro Leu Ser Asp Lys Asn Leu Val
                125                 130                 135

Ala Met Gly Cys Leu Asp Pro Asp
                140

<210> SEQ ID NO 8
<211> LENGTH: 141
<212> TYPE: PRT
<213> ORGANISM: Mus musculus
<220> FEATURE:
<223> OTHER INFORMATION: Sequence of framework three (FR3) region in
      hybridoma g04 incorporating VH7183.6 heavy chain gene from the
      VH7183 (MOPC21) family

<400> SEQUENCE: 8

Gly Gly Leu Val Gln Pro Gly Gly Ser Arg Lys Leu Ser Cys Ala
                5                   10                  15

Ala Ser Gly Phe Thr Phe Ser Ser Phe Gly Met His Trp Val Arg
                20                  25                  30

Gln Ala Pro Glu Lys Gly Leu Glu Trp Val Ala Tyr Ile Ser Ser
                35                  40                  45

Gly Ser Ser Thr Ile Tyr Tyr Ala Asp Thr Val Lys Gly Arg Phe
                50                  55                  60

Thr Ile Ser Arg Asp Asn Pro Lys Asn Thr Leu Phe Leu Gln Met
                65                  70                  75

Thr Ser Leu Arg Ser Glu Asp Thr Ala Met Tyr Tyr Cys Ala Thr
                80                  85                  90

```
Tyr Arg Phe Tyr Ala Met Asp Tyr Trp Gly Gln Gly Thr Ser Val
                95                 100                 105

Thr Val Ser Ser Glu Ser Gln Ser Phe Pro Asn Val Phe Pro Leu
                110                 115                 120

Val Ser Cys Glu Ser Pro Leu Ser Asp Lys Asn Leu Val Ala Met
                125                 130                 135

Gly Cys Leu Ala Arg Asp
                140

<210> SEQ ID NO 9
<211> LENGTH: 147
<212> TYPE: PRT
<213> ORGANISM: Mus musculus
<220> FEATURE:
<223> OTHER INFORMATION: Sequence of framework three (FR3) region in
      hybridoma g06 incorporating VH7183.6 heavy chain gene from the
      VH7183 (MOPC21) family

<400> SEQUENCE: 9

Gly Gly Leu Val Gln Pro Gly Gly Ser Arg Lys Leu Ser Cys Ala
                 5                  10                  15

Ala Ser Gly Phe Thr Phe Ser Ser Phe Gly Met His Trp Val Arg
                20                  25                  30

Leu Ala Pro Asp Lys Gly Leu Glu Trp Val Ala Tyr Ile Ser Ser
                35                  40                  45

Gly Ser Ser Thr Ile Tyr Tyr Ala Asp Thr Val Lys Gly Arg Phe
                50                  55                  60

Thr Ile Ser Arg Asp Asn Pro Lys Asn Thr Leu Phe Leu Gln Met
                65                  70                  75

Thr Ser Leu Arg Ser Asp Asp Thr Ala Met Tyr Tyr Cys Ala Arg
                80                  85                  90

Ser Gly His Asp Tyr Gly Tyr Ser Arg Gly Tyr Phe Asp Val Trp
                95                  100                 105

Gly Ala Gly Thr Thr Val Thr Val Ser Ser Glu Ser Gln Ser Phe
                110                 115                 120

Ser Asn Val Phe Pro Leu Val Ser Cys Glu Ser Pro Leu Ser Asp
                125                 130                 135

Lys Asn Leu Val Ala Met Gly Cys Leu Asp Pro Asp
                140                 145

<210> SEQ ID NO 10
<211> LENGTH: 147
<212> TYPE: PRT
<213> ORGANISM: Mus musculus
<220> FEATURE:
<223> OTHER INFORMATION: Sequence of framework three (FR3) region in
      hybridoma d06 incorporating VH7183.6 heavy chain gene from the
      VH7183 (MOPC21) family

<400> SEQUENCE: 10

Gly Gly Leu Val Gln Pro Gly Gly Ser Arg Lys Leu Ser Cys Ala
                 5                  10                  15

Ala Ser Gly Phe Thr Phe Ser Ser Phe Gly Met His Trp Val Arg
                20                  25                  30

Gln Ala Pro Glu Lys Gly Leu Glu Trp Val Ala Tyr Ile Ser Ser
                35                  40                  45

Gly Ser Ser Thr Ile Tyr Tyr Ala Asp Thr Val Lys Gly Arg Phe
                50                  55                  60

Thr Ile Ser Arg Asp Asn Pro Lys Asn Thr Leu Phe Leu Gln Met
                65                  70                  75
```

-continued

```
Thr Ser Leu Arg Ser Glu Asp Thr Ala Met Tyr Tyr Cys Ala Arg
                80                  85                  90

Ser Gly His Tyr Tyr Gly Tyr Ser Arg Gly Tyr Phe Asp Val Trp
                95                 100                 105

Gly Ala Gly Thr Thr Val Thr Val Ser Ser Ala Thr Thr Thr Ala
               110                 115                 120

Pro Ser Val Tyr Pro Leu Val Pro Gly Cys Ile Asp Thr Ser Gly
               125                 130                 135

Ser Ser Val Thr Leu Gly Cys Leu Val Lys Ala Thr
               140                 145

<210> SEQ ID NO 11
<211> LENGTH: 143
<212> TYPE: PRT
<213> ORGANISM: Mus musculus
<220> FEATURE:
<223> OTHER INFORMATION: Sequence of framework three (FR3) region in
      hybridoma a07 incorporating VH7183.6 heavy chain gene from the
      VH7183 (MOPC21) family

<400> SEQUENCE: 11

Gly Gly Leu Val Gln Pro Gly Gly Ser Arg Lys Leu Ser Cys Ala
                 5                  10                  15

Ala Ser Gly Phe Thr Phe Ser Ser Phe Gly Met His Trp Val Arg
                20                  25                  30

Gln Ala Pro Glu Lys Gly Leu Glu Trp Val Ala Tyr Ile Ser Ser
                35                  40                  45

Gly Ser Ser Thr Ile Tyr Tyr Ala Asp Thr Val Lys Gly Arg Phe
                50                  55                  60

Thr Ile Ser Arg Asp Asn Pro Lys Asn Thr Leu Phe Leu Gln Met
                65                  70                  75

Thr Ser Leu Arg Ser Glu Asp Thr Ala Met Tyr Tyr Cys Ala Lys
                80                  85                  90

Trp Glu Val Thr Thr Arg Tyr Phe Asp Val Trp Gly Ala Gly Thr
                95                 100                 105

Thr Val Thr Val Ser Ser Ala Thr Thr Thr Ala Pro Ser Val Tyr
               110                 115                 120

Pro Leu Val Pro Gly Cys Ser Asp Thr Ser Gly Ser Ser Val Thr
               125                 130                 135

Leu Gly Cys Leu Val Lys Ala Thr
               140

<210> SEQ ID NO 12
<211> LENGTH: 145
<212> TYPE: PRT
<213> ORGANISM: Mus musculus
<220> FEATURE:
<223> OTHER INFORMATION: Sequence of framework three (FR3) region in
      hybridoma e11 incorporating VH7183.6 heavy chain gene from the
      VH7183 (MOPC21) family

<400> SEQUENCE: 12

Gly Gly Leu Val Gln Pro Gly Gly Ser Arg Lys Leu Ser Cys Ala
                 5                  10                  15

Ala Ser Gly Phe Thr Phe Ser Ser Phe Gly Met His Trp Val Arg
                20                  25                  30

Gln Ala Pro Glu Lys Gly Leu Glu Trp Val Ala Tyr Ile Ser Ser
                35                  40                  45

Gly Ser Ser Thr Ile Tyr Tyr Ala Asp Thr Val Lys Gly Arg Phe
```

```
                            50                  55                  60

Thr Ile Ser Arg Asp Asn Pro Lys Asn Thr Leu Phe Leu Gln Met
                65                  70                  75

Thr Ser Leu Arg Ser Glu Asp Thr Ala Met Tyr Tyr Cys Ala Arg
                80                  85                  90

Tyr Asp Thr Thr Val Val Ala Arg Ala Met Asp Tyr Trp Gly Gln
                95                 100                 105

Gly Thr Ser Val Thr Val Ser Ser Ala Thr Thr Thr Ala Pro Ser
               110                 115                 120

Val Tyr Pro Leu Val Pro Gly Cys Ile Asp Thr Ser Gly Ser Ser
               125                 130                 135

Val Thr Leu Gly Cys Leu Val Lys Ala Thr
               140                 145

<210> SEQ ID NO 13
<211> LENGTH: 144
<212> TYPE: PRT
<213> ORGANISM: Mus musculus
<220> FEATURE:
<223> OTHER INFORMATION: Sequence of framework three (FR3) region in
      hybridoma a05 incorporating VH7183.6 heavy chain gene from the
      VH7183 (MOPC21) family

<400> SEQUENCE: 13

Gly Gly Leu Val Gln Pro Gly Gly Ser Arg Lys Leu Ser Cys Ala
                 5                  10                  15

Ala Ser Gly Phe Thr Phe Ser Thr Phe Gly Val His Trp Val Arg
                20                  25                  30

Gln Ala Pro Asp Lys Gly Leu Glu Trp Val Ala Tyr Ile Thr Ser
                35                  40                  45

Gly Ser Ser Thr Ile Tyr Tyr Ala Asp Thr Val Lys Gly Arg Phe
                50                  55                  60

Thr Ile Ser Arg Asp Asn Pro Lys Asn Thr Leu Phe Leu Gln Met
                65                  70                  75

Thr Ser Leu Thr Ser Glu Asp Thr Ala Met Tyr Tyr Cys Ala Arg
                80                  85                  90

Arg Asn Cys Gly Ser Lys Arg Ala Ile Asp Tyr Trp Gly Gln Gly
                95                 100                 105

Thr Ser Val Thr Val Ser Ser Ala Thr Thr Thr Ala Pro Ser Val
               110                 115                 120

Tyr Pro Leu Val Pro Gly Cys Ser Asp Thr Ser Gly Ser Ser Val
               125                 130                 135

Thr Leu Gly Cys Leu Val Lys Ala Thr
               140

<210> SEQ ID NO 14
<211> LENGTH: 142
<212> TYPE: PRT
<213> ORGANISM: Mus musculus
<220> FEATURE:
<223> OTHER INFORMATION: Sequence of framework three (FR3) region in
      hybridoma e07 incorporating VH7183.6 heavy chain gene from the
      VH7183 (MOPC21) family

<400> SEQUENCE: 14

Gly Gly Leu Val Gln Pro Gly Gly Ser Arg Lys Leu Ser Cys Ala
                 5                  10                  15

Ala Ser Gly Phe Thr Phe Ser Thr Phe Gly Met His Trp Val Arg
                20                  25                  30
```

Gln Ala Pro Glu Lys Gly Leu Glu Trp Val Ala Tyr Ile Ser Ser
              35                  40                  45

Gly Ser Ser Thr Ile Tyr Tyr Ala Asp Thr Val Lys Gly Arg Phe
              50                  55                  60

Thr Ile Ser Arg Asp Asn Pro Lys Asn Thr Leu Phe Leu Gln Met
              65                  70                  75

Thr Asn Leu Thr Ser Glu Asp Thr Ala Met Tyr Tyr Cys Ala Arg
              80                  85                  90

Trp Asp Ala Leu Arg Thr Phe Ala Tyr Trp Gly Gln Gly Thr Leu
              95                 100                 105

Val Thr Val Ser Ala Ala Lys Thr Thr Ala Pro Ser Val Tyr Pro
             110                 115                 120

Leu Ala Pro Val Cys Gly Asp Thr Thr Gly Ser Ser Val Thr Leu
             125                 130                 135

Gly Cys Leu Val Lys Gly Tyr
             140

<210> SEQ ID NO 15
<211> LENGTH: 141
<212> TYPE: PRT
<213> ORGANISM: Mus musculus
<220> FEATURE:
<223> OTHER INFORMATION: Sequence of framework three (FR3) region in
      hybridoma d12 incorporating VH7183.6 heavy chain gene from the
      VH7183 (MOPC21) family

<400> SEQUENCE: 15

Gly Gly Leu Val Gln Pro Gly Gly Ser Arg Lys Leu Ser Cys Ala
              5                   10                  15

Ala Ser Gly Phe Thr Phe Ser Ser Phe Gly Met His Trp Val Arg
              20                  25                  30

Gln Ala Pro Glu Lys Gly Leu Glu Trp Val Ala Tyr Ile Ser Ser
              35                  40                  45

Gly Ser Ser Thr Ile Tyr Tyr Ala Asp Thr Val Lys Gly Arg Phe
              50                  55                  60

Thr Ile Ser Arg Asp Asn Pro Lys Asn Thr Leu Phe Leu Gln Met
              65                  70                  75

Thr Ser Leu Thr Ser Glu Asp Thr Ala Met Tyr Tyr Cys Ala Arg
              80                  85                  90

Trp Leu Leu Arg Ala Met Asp Tyr Trp Gly Gln Gly Thr Ser Val
              95                 100                 105

Thr Val Ser Ser Ala Lys Thr Thr Ala Pro Ser Val Tyr Pro Leu
             110                 115                 120

Ala Pro Val Cys Gly Asp Thr Thr Gly Ser Ser Val Thr Leu Arg
             125                 130                 135

Cys Leu Val Lys Gly Tyr
             140

<210> SEQ ID NO 16
<211> LENGTH: 147
<212> TYPE: PRT
<213> ORGANISM: Mus musculus
<220> FEATURE:
<223> OTHER INFORMATION: Sequence of framework three (FR3) region in
      hybridoma d04 incorporating VH7183.6 heavy chain gene from the
      VH7183 (MOPC21) family

<400> SEQUENCE: 16

Gly Gly Leu Val Gln Pro Gly Gly Ser Arg Lys Leu Ser Cys Ala
              5                   10                  15

Ala Ser Gly Phe Thr Phe Ser Thr Phe Gly Met His Trp Val Arg
            20                  25                  30

Gln Ala Pro Glu Lys Gly Leu Glu Trp Val Ala Tyr Ile Ser Ser
            35                  40                  45

Gly Ser Ser Thr Ile Tyr Tyr Ala Asp Thr Val Lys Gly Arg Phe
            50                  55                  60

Thr Ile Ser Arg Asp Asn Pro Lys Asn Thr Leu Phe Leu Gln Met
            65                  70                  75

Thr Ser Leu Thr Ser Glu Asp Thr Ala Met Tyr Tyr Cys Ala Arg
            80                  85                  90

Trp His Tyr Tyr Gly Thr Asn Tyr Val Arg Ala Met Asp Tyr Trp
            95                 100                 105

Gly Gln Gly Thr Ser Val Thr Val Ser Ser Ala Lys Thr Thr Ala
           110                 115                 120

Pro Ser Val Tyr Pro Leu Ala Pro Gly Cys Gly Asp Thr Thr Gly
           125                 130                 135

Ser Ser Leu Thr Leu Gly Cys Leu Val Asn Gly Tyr
           140                 145

<210> SEQ ID NO 17
<211> LENGTH: 147
<212> TYPE: PRT
<213> ORGANISM: Mus musculus
<220> FEATURE:
<223> OTHER INFORMATION: Sequence of framework three (FR3) region in
      hybridoma f10 incorporating VH7183.6 heavy chain gene from the
      VH7183 (MOPC21) family

<400> SEQUENCE: 17

Gly Gly Leu Val Gln Pro Gly Gly Ser Arg Lys Leu Ser Cys Ala
             5                  10                  15

Ala Ser Gly Phe Thr Phe Ser Thr Phe Gly Met His Trp Val Arg
            20                  25                  30

Gln Ala Pro Glu Lys Gly Leu Glu Trp Val Ala Tyr Ile Ser Ser
            35                  40                  45

Gly Ser Ser Thr Ile Tyr Tyr Ala Asp Thr Val Lys Gly Arg Phe
            50                  55                  60

Thr Ile Ser Arg Asp Asn Pro Lys Asn Thr Leu Phe Leu Gln Met
            65                  70                  75

Thr Ser Leu Thr Ser Glu Asp Thr Ala Met Tyr Tyr Cys Ala Arg
            80                  85                  90

His Tyr Arg Tyr Asp Glu Gly Pro His Trp Tyr Phe Asp Val Trp
            95                 100                 105

Gly Ala Gly Thr Thr Val Thr Val Ser Ser Ala Lys Thr Thr Ser
           110                 115                 120

Pro Ser Val Tyr Pro Leu Ala Pro Gly Cys Gly Asp Thr Thr Gly
           125                 130                 135

Ser Ser Val Thr Leu Gly Cys Leu Val Lys Gly Tyr
           140                 145

<210> SEQ ID NO 18
<211> LENGTH: 7
<212> TYPE: PRT
<213> ORGANISM: Mus musculus
<220> FEATURE:
<223> OTHER INFORMATION: VH gene sequence of monoclonal antibody 2
      against Bacillus anthracis spores

<400> SEQUENCE: 18

Thr Tyr Pro Ile Pro Arg
            5

<210> SEQ ID NO 19
<211> LENGTH: 7
<212> TYPE: PRT
<213> ORGANISM: Mus musculus
<220> FEATURE:
<223> OTHER INFORMATION: VH gene sequence of monoclonal antibody 3
      against Bacillus anthracis spores

<400> SEQUENCE: 19

Thr Tyr Pro Ile Pro Phe Arg
            5

<210> SEQ ID NO 20
<211> LENGTH: 7
<212> TYPE: PRT
<213> ORGANISM: Mus musculus
<220> FEATURE:
<223> OTHER INFORMATION: VH gene sequence of monoclonal antibody 4
      against Bacillus anthracis spores

<400> SEQUENCE: 20

Thr Tyr Pro Val Pro His Arg
            5

<210> SEQ ID NO 21
<211> LENGTH: 139
<212> TYPE: PRT
<213> ORGANISM: Mus musculus
<220> FEATURE:
<223> OTHER INFORMATION: VH gene sequence of monoclonal antibody 9-1
      against Bacillus anthracis spores

<400> SEQUENCE: 21

Pro Ser Gln Ser Leu Ser Ile Thr Cys Thr Val Ser Gly Phe Ser
            5                   10                  15

Leu Ser Gly Tyr Ser Val His Trp Val Arg Gln Arg Pro Gly Lys
            20                  25                  30

Gly Leu Glu Cys Leu Gly Met Ile Trp Gly Val Gly Ser Thr Asp
            35                  40                  45

Tyr Asn Ser Ala Leu Lys Ser Arg Leu Ser Ile Ser Lys Asp Asn
            50                  55                  60

Ser Lys Ser Gln Val Phe Leu Lys Met Asn Ser Leu Gln Thr Asp
            65                  70                  75

Asp Thr Ala Met Tyr Tyr Cys Ala Arg Asp Tyr Tyr Gly Asn Tyr
            80                  85                  90

Val Trp Tyr Phe Asp Val Trp Gly Ala Gly Thr Thr Val Thr Val
            95                  100                 105

Ser Ser Ala Lys Thr Thr Pro Pro Ser Val Tyr Pro Leu Ala Pro
            110                 115                 120

Gly Cys Gly Asp Thr Thr Gly Ser Ser Val Thr Leu Gly Cys Leu
            125                 130                 135

Val Lys Gly Tyr

<210> SEQ ID NO 22
<211> LENGTH: 129
<212> TYPE: PRT
<213> ORGANISM: Mus musculus
<220> FEATURE:
<223> OTHER INFORMATION: VH gene sequence of monoclonal antibody 7-1
      against Bacillus anthracis spores

```
<400> SEQUENCE: 22

Phe Thr Phe Thr Asn Tyr Tyr Met Ser Trp Val Arg Gln Pro Pro
                 5                  10                  15

Gly Lys Ala Leu Glu Trp Leu Gly Phe Ile Ile Asn Lys Ala Asn
             20                  25                  30

Gly Tyr Thr Thr Glu Tyr Ser Ala Ser Val Lys Gly Arg Phe Thr
         35                  40                  45

Ile Ser Arg Asp Asn Ser Gln Ser Ile Leu Tyr Leu Gln Met Asn
     50                  55                  60

Thr Leu Arg Ala Glu Asp Ser Ala Thr Tyr Tyr Cys Ala Arg Ala
 65                  70                  75

Tyr Tyr Gly Asn Tyr Pro Ala Trp Phe Ala Tyr Trp Gly Gln Gly
                 80                  85                  90

Thr Leu Val Thr Val Ser Ala Ala Lys Thr Thr Ala Pro Ser Val
             95                 100                 105

Tyr Gln Leu Ala Pro Val Cys Gly Asp Thr Thr Gly Ser Ser Val
        110                 115                 120

Thr Leu Gly Cys Leu Val Lys Gly Tyr
                125

<210> SEQ ID NO 23
<211> LENGTH: 143
<212> TYPE: PRT
<213> ORGANISM: Mus musculus
<220> FEATURE:
<223> OTHER INFORMATION: VH gene sequence of monoclonal antibody 24-2
      against Bacillus anthracis spores

<400> SEQUENCE: 23

Gly Gly Leu Val Lys Pro Gly Gly Ser Leu Lys Leu Ser Cys Ala
                 5                  10                  15

Ala Ser Gly Phe Thr Phe Ser Ser Tyr Ala Met Ser Trp Val Arg
             20                  25                  30

Gln Thr Pro Glu Lys Arg Leu Glu Trp Val Ala Thr Ile Ser Ser
         35                  40                  45

Gly Gly Ser Tyr Thr Tyr Tyr Pro Asp Ser Val Lys Gly Arg Phe
     50                  55                  60

Thr Ile Ser Arg Asp Asn Ala Lys Asn Thr Leu Tyr Leu Gln Met
 65                  70                  75

Ser Ser Leu Arg Ser Glu Asp Thr Ala Met Tyr Tyr Cys Ala Arg
                 80                  85                  90

Gln Gly Leu Arg Arg Tyr Ala Met Asp Tyr Trp Gly Gln Gly Thr
             95                 100                 105

Ser Val Thr Val Ser Ser Ala Lys Thr Thr Pro Pro Ser Val Tyr
        110                 115                 120

Pro Leu Ala Pro Gly Phe Gly Asp Thr Thr Gly Ser Ser Val Thr
                125                 130                 135

Leu Gly Cys Leu Val Lys Gly Tyr
                140

<210> SEQ ID NO 24
<211> LENGTH: 142
<212> TYPE: PRT
<213> ORGANISM: Mus musculus
<220> FEATURE:
<223> OTHER INFORMATION: VH gene sequence of monoclonal antibody 21-4
      against Bacillus anthracis spores
```

-continued

```
<400> SEQUENCE: 24

Gly Gly Leu Val Lys Pro Ala Gly Ser Leu Lys Leu Ser Cys Ala
                  5                  10                  15

Ala Ser Gly Phe Thr Phe Ser Ser Tyr Ala Met Ser Trp Val Arg
                 20                  25                  30

Gln Thr Pro Glu Lys Arg Leu Glu Trp Val Ala Thr Ile Ser Ser
                 35                  40                  45

Gly Gly Ser Tyr Thr Tyr Tyr Pro Asp Ser Val Lys Gly Arg Phe
                 50                  55                  60

Thr Ile Ser Ile Asp Asn Ala Lys Asn Thr Leu Tyr Leu Gln Met
                 65                  70                  75

Ser Ser Leu Arg Ser Glu Asp Thr Ala Met Tyr Tyr Cys Ala Arg
                 80                  85                  90

Gln Gly Leu Arg Arg Val Ala Met Asp Tyr Trp Gly Gln Gly Thr
                 95                 100                 105

Ser Val Thr Val Ser Ser Ala Lys Thr Thr Ala Pro Ser Val Tyr
                110                 115                 120

Gln Leu Ala Pro Gly Phe Gly Asp Thr Thr Gly Ser Ser Val Thr
                125                 130                 135

Leu Gly Cys Leu Val Lys Gly
                140

<210> SEQ ID NO 25
<211> LENGTH: 141
<212> TYPE: PRT
<213> ORGANISM: Mus musculus
<220> FEATURE:
<223> OTHER INFORMATION: VH gene sequence of monoclonal antibody 10-2
      against Bacillus anthracis spores

<400> SEQUENCE: 25

Gly Gly Leu Val Lys Pro Trp Arg Ser Leu Lys Phe Ser Cys Ala
                  5                  10                  15

Ala Ser Gly Phe Thr Phe Ser Ser Tyr Ala Met Pro Trp Val Arg
                 20                  25                  30

Gln Thr Pro Glu Lys Arg Leu Glu Trp Val Ala Thr Ile Arg Ser
                 35                  40                  45

Gly Gly Ser Tyr Thr Tyr Tyr Pro Asp Ser Val Lys Gly Arg Phe
                 50                  55                  60

Thr Ile Ser Arg Asp Asn Ala Lys Asn Thr Leu Tyr Leu Gln Met
                 65                  70                  75

Ser Ser Leu Arg Ser Glu Asp Thr Ala Met Tyr Tyr Cys Pro Ile
                 80                  85                  90

Tyr Asp Gly His Ala Met Asp Tyr Trp Gly Gln Gly Thr Ser Val
                 95                 100                 105

Thr Val Ser Ser Ala Thr Thr Thr Ala Pro Ser Val Tyr Pro Leu
                110                 115                 120

Val Pro Gly Cys Ala Asp Thr Thr Gly Ser Ser Val Thr Leu Gly
                125                 130                 135

Cys Leu Val Lys Gly Tyr
                140

<210> SEQ ID NO 26
<211> LENGTH: 145
<212> TYPE: PRT
<213> ORGANISM: Mus musculus
<220> FEATURE:
<223> OTHER INFORMATION: VH gene sequence of monoclonal antibody 22-1
``` against Bacillus anthracis spores

<400> SEQUENCE: 26

```
Gly Asp Leu Val Lys Pro Gly Gly Ser Leu Lys Leu Ser Cys Ala
                 5                  10                  15

Ala Ser Gly Phe Thr Phe Ser Ser Tyr Gly Met Ser Trp Val Arg
                20                  25                  30

Gln Thr Pro Asp Lys Arg Leu Glu Trp Val Ala Thr Ile Ser Ser
                35                  40                  45

Gly Gly Ser Tyr Thr Tyr Tyr Pro Asp Ser Val Lys Gly Arg Phe
                50                  55                  60

Thr Ile Ser Arg Asp Asn Ala Lys Asn Thr Leu Tyr Leu Gln Met
                65                  70                  75

Ser Ser Leu Lys Ser Glu Asp Thr Ala Met Tyr Tyr Cys Ala Arg
                80                  85                  90

Arg Gly Ile Thr Thr Ala Ile Tyr Ala Met Asp Tyr Trp Gly Gln
                95                  100                 105

Gly Thr Ser Val Thr Val Ser Ser Glu Ser Gln Ser Phe Pro Asn
                110                 115                 120

Val Phe Pro Leu Val Ser Cys Glu Ser Pro Leu Ser Asp Lys Asn
                125                 130                 135

Leu Val Ala Met Gly Cys Leu Ala Arg Asp
                140                 145
```

<210> SEQ ID NO 27
<211> LENGTH: 142
<212> TYPE: PRT
<213> ORGANISM: Mus musculus
<220> FEATURE:
<223> OTHER INFORMATION: VH gene sequence of monoclonal antibody 13-3
      against Bacillus anthracis spores

<400> SEQUENCE: 27

```
Ala Glu Leu Ala Arg Pro Gly Pro Ser Val Lys Met Ser Cys Lys
                 5                  10                  15

Ala Ser Gly Tyr Thr Phe Thr Arg Tyr Thr Met His Trp Val Lys
                20                  25                  30

Gln Arg Pro Gly Gln Gly Leu Glu Trp Ile Gly Tyr Ile Asn Pro
                35                  40                  45

Ser Ser Gly Tyr Thr Asn Tyr Asn Gln Lys Phe Lys Asp Lys Ala
                50                  55                  60

Thr Leu Thr Ala Asp Lys Ser Ser Arg Thr Ala Tyr Met Gln Leu
                65                  70                  75

Ser Ser Leu Thr Ser Glu Asp Ser Ala Val Tyr Tyr Cys Ala Arg
                80                  85                  90

Val Thr Ala Arg Tyr Ala Met Asp Tyr Trp Gly Gln Gly Thr Ser
                95                  100                 105

Val Thr Val Ser Ser Ala Lys Thr Thr Ala Pro Ser Val Tyr Pro
                110                 115                 120

Leu Ala Pro Val Cys Gly Asp Thr Thr Gly Ser Ser Val Thr Leu
                125                 130                 135

Gly Cys Leu Val Lys Gly Tyr
                140
```

<210> SEQ ID NO 28
<211> LENGTH: 140
<212> TYPE: PRT
<213> ORGANISM: Mus musculus

```
<220> FEATURE:
<223> OTHER INFORMATION: VH gene sequence of monoclonal antibody 8-3
      against Bacillus anthracis spores

<400> SEQUENCE: 28

Gly Ala Glu Leu Val Arg Pro Gly Thr Ser Val Lys Met Ser Cys
                  5                  10                  15

Lys Ala Ala Gly Tyr Thr Phe Thr Asn Tyr Trp Ile Gly Trp Val
                 20                  25                  30

Lys Gln Arg Pro Gly His Gly Leu Glu Trp Ile Gly Asp Ile Tyr
                 35                  40                  45

Pro Gly Gly Gly Tyr Thr Asn Tyr Asn Glu Lys Phe Lys Gly Lys
                 50                  55                  60

Ala Thr Leu Thr Ala Asp Thr Ser Ser Thr Ala Tyr Met Gln
                 65                  70                  75

Leu Ser Ser Leu Thr Ser Glu Asp Ser Ala Ile Tyr Tyr Cys Ala
                 80                  85                  90

Arg Gly Asn Leu Gly Asp Tyr Trp Gly Gln Gly Thr Thr Leu Thr
                 95                 100                 105

Val Ser Ser Ala Lys Thr Thr Ala Pro Ser Val Tyr Pro Leu Ala
                110                 115                 120

Pro Val Cys Gly Asp Thr Thr Gly Ser Ser Val Thr Leu Gly Cys
                125                 130                 135

Leu Val Lys Gly Tyr
                140

<210> SEQ ID NO 29
<211> LENGTH: 141
<212> TYPE: PRT
<213> ORGANISM: Mus musculus
<220> FEATURE:
<223> OTHER INFORMATION: VH gene sequence of monoclonal antibody 6-1
      against Bacillus anthracis spores

<400> SEQUENCE: 29

Glu Leu Gly Ala Ser Val Lys Leu Ser Cys Lys Ala Ser Gly Tyr
                  5                  10                  15

Thr Phe Thr Ser Tyr Trp Met His Trp Val Lys Leu Arg His Gly
                 20                  25                  30

Gln Gly Leu Glu Trp Ile Gly Asn Ile Tyr Pro Gly Ser Gly Ser
                 35                  40                  45

Thr Asn Tyr Asp Glu Lys Phe Lys Asp Lys Gly Thr Leu Thr Val
                 50                  55                  60

Asp Thr Ser Ser Ser Thr Ala Tyr Met His Leu Ser Ser Leu Thr
                 65                  70                  75

Ser Glu Asp Ser Ala Val Tyr Tyr Cys Thr Arg Lys Gly Arg Gly
                 80                  85                  90

Ser Gly Tyr Asp Thr Met Asp Tyr Trp Gly Gln Gly Thr Ser Val
                 95                 100                 105

Thr Val Ser Ser Ala Lys Thr Thr Ala Pro Ser Val Tyr Pro Leu
                110                 115                 120

Ala Pro Val Cys Gly Asp Thr Thr Gly Ser Ser Val Thr Val Gly
                125                 130                 135

Cys Leu Val Lys Gly Tyr
                140

<210> SEQ ID NO 30
<211> LENGTH: 146
```

```
<212> TYPE: PRT
<213> ORGANISM: Mus musculus
<220> FEATURE:
<223> OTHER INFORMATION: VH gene sequence of monoclonal antibody 3-1
      against Bacillus anthracis spores

<400> SEQUENCE: 30

Gly Ala Glu Leu Ala Lys Pro Gly Ala Ser Val Lys Met Ser Cys
                  5                  10                  15

Lys Ala Ser Gly Tyr Thr Phe Thr Ser Tyr Trp Met His Trp Val
                 20                  25                  30

Lys Gln Arg Pro Gly Gln Gly Leu Glu Trp Ile Gly Asn Ile Asn
                 35                  40                  45

Pro Ser Pro Gly Tyr Thr Glu Tyr Asn Gln Lys Phe Lys Asp Lys
                 50                  55                  60

Gly Thr Leu Thr Ala Asp Lys Ser Ser Ser Thr Ala Tyr Met Gln
                 65                  70                  75

Leu Ser Ser Leu Thr Ser Glu Asp Ser Ala Val Tyr Tyr Cys Ala
                 80                  85                  90

Arg Ile Gly Ser Gly Tyr Val Gly Tyr Ala Met Asp Tyr Trp Gly
                 95                 100                 105

Gln Gly Thr Ser Val Thr Val Ser Ser Glu Ser Gln Ser Phe Pro
                110                 115                 120

Asn Val Phe Pro Leu Val Ser Cys Glu Ser Pro Leu Ser Glu Lys
                125                 130                 135

Gln Leu Val Ala Met Gly Cys Leu Ala Arg Asp
                140                 145

<210> SEQ ID NO 31
<211> LENGTH: 7
<212> TYPE: PRT
<213> ORGANISM: Mus musculus
<220> FEATURE:
<223> OTHER INFORMATION: VH gene sequence of monoclonal antibody 1
      against Bacillus anthracis spores

<400> SEQUENCE: 31

Thr Ser Gln Asn Val Arg Thr
                  5
```